United States Patent
Grossman et al.

(10) Patent No.: US 7,250,430 B2
(45) Date of Patent: Jul. 31, 2007

(54) THIOPHENE-AND THIAZOLESULFONAMIDES AS ANTINEOPLASTIC AGENTS

(75) Inventors: Cora Sue Grossman, Indianapolis, IN (US); Philip Arthur Hipskind, New Palestine, IN (US); Ho-Shen Lin, Indianapolis, IN (US); Karen Lynn Lobb, Indianapolis, IN (US); Beatriz Lopez de Uralde Garmendia, Madrid (ES); Jose Eduardo Lopez, Fishers, IN (US); Mary Margaret Mader, Fishers, IN (US); Michael Enrico Richett, Indianapolis, IN (US); Chuan Shih, Carmel, IN (US); Alfonso De Dios, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 11/447,457

(22) Filed: Jun. 6, 2006

(65) Prior Publication Data

US 2006/0223871 A1    Oct. 5, 2006

(51) Int. Cl.
*A61K 31/381*   (2006.01)
*A61K 31/426*   (2006.01)
(52) U.S. Cl. .................... 514/369; 514/445

(58) Field of Classification Search ........... 514/445, 514/369
See application file for complete search history.

(56) References Cited

U.S. PATENT DOCUMENTS 5,302,724 A    4/1994   Howbert et al.

FOREIGN PATENT DOCUMENTS

| EP | 0 42 731 A1 | 12/1981 |
| EP | 0 513 979 A | 11/1992 |
| EP | 0 560 554 A | 9/1993 |
| WO | WO 98 14440 A | 4/1998 |

*Primary Examiner*—Laura L. Stockton
(74) *Attorney, Agent, or Firm*—Tina M. Tucker; Robert D. Titus

(57) ABSTRACT

The present invention provides antineoplastic compounds of the formula:

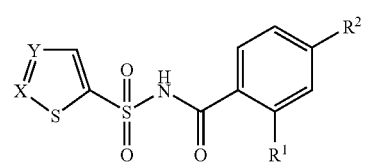

and antineoplastic methods.

6 Claims, No Drawings

THIOPHENE-AND THIAZOLESULFONAMIDES AS ANTINEOPLASTIC AGENTS

In recent years fundamental advances have been made in the development of chemical agents and regimens of therapy to combat neoplastic diseases. Despite these continuing advances, cancers continue to exact intolerable levels of human pain and suffering. The need for new and better methods of treating malignant neoplasms and leukemias continues to fuel efforts to create new classes of compounds, especially in the area of inoperable or metastatic solid tumors. The recent avalanche of information regarding the basic biological processes involved in neoplasms has led to a deeper understanding of the heterogeneity of tumors. It is because of this extreme heterogeneity among populations of neoplastic cells that new chemotherapeutic agents should have a wide spectrum of activity and an acceptable therapeutic index. In addition, such agents must be chemically stable and compatible with other agents. It is also important that any chemotherapeutic regimen be as convenient and painless as possible to the patient.

Chemotherapy and radiation are frequently used in the treatment of cancer and, although they often produce some response in the malignant disease, they are rarely curative. Most solid tumors increase in mass through the proliferation of malignant cells and stromal cells, including endothelial cells. In order for a tumor to grow larger than 2-3 millimeters in diameter, it must form a vasculature, a process known as angiogenesis. Suppression of tumor-induced angiogenesis by angiostatin and endostatin has been reported to result in antitumor activity (O'Reilly, et al., Cell, 88, 277-285 (1997)). Because angiogenesis is a critical component of the mass expansion of most solid tumors, the development of new agents for the inhibition of this process represents a promising approach for antitumor therapy. This approach to antitumor therapy may lack the toxic side effects or drug resistance-inducing properties of conventional chemotherapy (Judah Folkman, *Endogenous Inhibitors of Angiogenesis*, The Harvey Lectures, Series 92, pages 65-82, Wiley-Liss Inc., (1998)).

The present invention provides novel N-[benzoyl]-heteroarylsulfonamide compounds useful in the treatment of susceptible neoplasms.

The present invention provides compounds of Formula I:

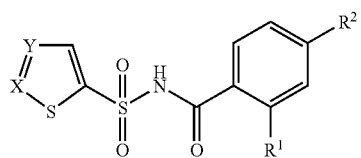

where:

—X=Y— is:

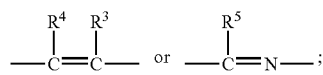

$R^1$ is selected from the group consisting of halo, $C_1$-$C_6$ alkyl, and $CF_3$;

$R^2$ is selected from the group consisting of halo, —$NO_2$, $C_1$-$C_6$ alkyl, and $CF_3$;

$R^3$ is hydrogen, $C_1$-$C_6$ alkyl, $C_1$-$C_4$ alkoxy, $C_1$-$C_6$ alkylthio, or halo;

$R^4$ is selected from the group consisting of hydrogen, halo, $C_1$-$C_4$ alkoxy, $C_1$-$C_6$ alkyl, —$COO(C_1$-$C_6$ alkyl), $C_1$-$C_6$ alkyl optionally substituted with $C_1$-$C_4$ alkoxy, cyano, $C_1$-$C_6$ alkylthio, $CF_3$, S-phenyl, and pyridinyl;

$R^5$ is halo, $C_1$-$C_6$ alkyl, or $C_1$-$C_4$ alkoxy; or a pharmaceutically acceptable base addition salt thereof.

The present invention further provides a method of treating susceptible neoplasms, in a mammal comprising administering to a mammal in need of such treatment an oncolytically effective amount of a compound of Formula I or a pharmaceutically acceptable base addition salt thereof.

The present invention also provides a method of suppressing tumor angiogenesis in a mammal comprising administering to a mammal in need of such treatment an angiogenesis suppressing amount of a compound of Formula I or a pharmaceutically acceptable base addition salt thereof.

The present invention also provides a pharmaceutical formulation comprising a compound of Formula I or a pharmaceutically acceptable base addition salt thereof and one or more pharmaceutically acceptable excipients.

This invention also provides the use of a compound of Formula I for the manufacture of a medicament for the treatment of susceptible neoplasms. Additionally, this invention provides a pharmaceutical formulation for the treatment susceptible neoplasms containing a compound of Formula I with a pharmaceutically acceptable carrier or excipient. Furthermore, this invention includes a method for the treatment of susceptible neoplasms that comprises administering an effective amount of a compound of Formula I.

The general chemical terms used in the formulae above have their usual meanings. For example, the term "$C_1$-$C_6$ alkyl" includes methyl, ethyl, propyl, isopropyl, butyl, isobutyl, sec-butyl, tert-butyl, pentyl, and hexyl moieties. The term "$C_1$-$C_4$ alkyl" is included within the meaning of $C_1$-$C_6$ alkyl and is taken to mean methyl, ethyl, propyl, isopropyl, butyl, sec-butyl, isobutyl and tert-butyl. The term "$C_1$-$C_4$ alkoxy" is taken to mean a $C_1$-$C_4$ alkyl group linked to the parent molecule through an oxygen atom, and includes the groups methoxy, ethoxy, isopropoxy, and the like. The term "halo" is taken to mean chlorine, bromine, fluorine, or iodine.

The term "mammal" is taken to mean any of various warm-blooded vertebrate animals of the class Mammalia, most preferably humans, characterized by a covering of hair on the skin and, in the female, milk-producing mammary glands for nourishing the young.

While all of the compounds of Formula I are useful antineoplastic agents, certain classes of compounds are preferred. The following paragraphs describe such preferred classes.

a) $R^1$ is halo, $C_1$-$C_6$ alkyl, or $CF_3$;
b) $R^1$ is chloro, bromo, fluoro, methyl, or $CF_3$;
c) $R^1$ is halo or $C_1$-$C_6$ alkyl;
d) $R^1$ is chloro;
e) $R^1$ is bromo;
f) $R^1$ is methyl;
g) $R^1$ is $CF_3$;
h) $R^2$ is halo, nitro, $C_1$-$C_6$ alkyl, or $CF_3$;
i) $R^2$ is chloro, bromo, nitro, methyl, or $CF_3$;
j) $R^2$ is halo or $C_1$-$C_6$ alkyl;
k) $R^2$ is chloro;

l) $R^2$ is bromo;
m) $R^2$ is methyl;
n) $R^2$ is $NO_2$;
o) $R^2$ is $CF_3$;
p) —X=Y— is

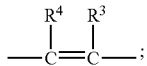

q) —X=Y— is

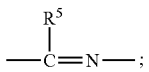

r) $R^3$ is H, halo, $C_1$-$C_6$ alkyl, $C_1$-$C_4$ alkoxy, or $C_1$-$C_6$ alkylthio;
s) $R^3$ is H, chloro, bromo, methyl, methoxy, or methylthio;
t) $R^3$ is H or halo;
u) $R^3$ is H;
v) $R^3$ is bromo;
w) $R^3$ is chloro;
x) $R^3$ is $C_1$-$C_6$ alkyl;
y) $R^3$ is methyl;
z) $R^3$ is $C_1$-$C_4$ alkoxy;
aa) $R^3$ is methoxy;
bb) $R^3$ is $C_1$-$C_6$ alkylthio;
cc) $R^3$ is methylthio;
dd) $R^4$ is H, halo, $C_1$-$C_6$ alkyl, $C_1$-$C_6$ alkylthio, $C_1$-$C_6$ alkyl optionally substituted with $C_1$-$C_4$ alkoxy, $C_1$-$C_4$ alkoxy, cyano, S-phenyl, or pyridinyl;
ee) $R^4$ is H, chloro, bromo, methyl, ethyl, propyl, methylthio, $CH_2OCH_3$, methoxy, cyano, S-phenyl, or pyridinyl;
ff) $R^4$ is $C_1$-$C_6$ alkyl;
gg) $R^4$ is methyl;
hh) $R^4$ is ethyl;
ii) $R^4$ is propyl;
jj) $R^4$ is halo;
kk) $R^4$ is chloro;
ll) $R^4$ is bromo;
mm) $R^4$ is hydrogen;
nn) $R^4$ is $C_1$-$C_4$ alkoxy;
oo) $R^4$ is methoxy;
pp) $R^4$ is —COO($C_1$-$C_6$ alkyl);
qq) $R^4$ is $C_1$-$C_6$ alkyl optionally substituted with $C_1$-$C_4$ alkoxy;
rr) $R^4$ is $CH_2OCH_3$;
ss) $R^4$ is cyano;
tt) $R^4$ is $C_1$-$C_6$ alkylthio;
uu) $R^4$ is S-phenyl;
vv) $R^4$ is pyridinyl;
ww) $R^5$ is halo;
xx) $R^5$ is chloro;
yy) $R^5$ is $C_1$-$C_4$ alkoxy;
zz) $R^5$ is methoxy;
aaa) $R^5$ is $C_1$-$C_6$ alkyl;
bbb) $R^5$ is methyl;
ccc) $R^1$ and $R^2$ are independently halo or $C_1$-$C_6$ alkyl;
ddd) $R^1$ and $R^2$ are chloro, bromo, or $R^1$ is methyl and $R^2$ is chloro;
eee) $R^1$ and $R^2$ are chloro;
fff) $R^1$ is methyl and $R^2$ is chloro;

It will be understood that the above classes may be combined to form additional preferred classes.

The compounds of Formula I are antineoplastic agents. Thus, the present invention also provides a method of treating a susceptible neoplasm in a mammal that comprises administering to a mammal in need of said treatment an oncolytically effective amount of a compound of Formula I. The present compounds are believed to be useful in treating susceptible neoplasms, including tumors and carcinomas, such as neoplasms of the central nervous system: glioblastoma multiforme, astrocytoma, oligodendroglial tumors, ependymal and choroid plexus tumors, pineal tumors, neuronal tumors, medulloblastoma, schwannoma, meningioma, meningeal sarcoma; neoplasms of the eye: basal cell carcinoma, squamous cell carcinoma, melanoma, rhabdomyosarcoma, retinoblastoma; neoplasms of the endocrine glands: pituitary neoplasms, neoplasms of the thyroid, neoplasms of the adrenal cortex, neoplasms of the neuroendocrine system, neoplasms of the gastroenteropancreatic endocrine system, neoplasms of the gonads; neoplasms of the head and neck: head and neck cancer, oral cavity, pharynx, larynx, odontogenic tumors; neoplasms of the thorax: large cell lung carcinoma, small cell lung carcinoma, non-small cell lung carcinoma, malignant mesothelioma, thymomas, primary germ cell tumors of the thorax; neoplasms of the alimentary canal: neoplasms of the esophagus, neoplasms of the stomach, neoplasms of the liver, neoplasms of the gallbladder, neoplasms of the exocrine pancreas, neoplasms of the small intestine, veriform appendix and peritoneum, adneocarcinoma of the colon and rectum, neoplasms of the anus; neoplasms of the genitourinary tract: renal cell carcinoma, neoplasms of the renal pelvis and ureter, neoplasms of the bladder, neoplasms of the urethra, neoplasms of the prostate, neoplasms of the penis, neoplasms of the testis; neoplasms of the female reproductive organs: neoplasms of the vulva and vagina, neoplasms of the cervix, addenocarcinoma of the uterine corpus, ovarian cancer, gynecologic sarcomas; neoplasms of the breast; neoplasms of the skin: basal cell carcinoma, squamous cell carcinoma, dermatofibrosarcoma, Merkel cell tumor; malignant melanoma; neoplasms of the bone and soft tissue: osteogenic sarcoma, malignant fibrous histiocytoma, chondrosarcoma, Ewing's sarcoma, primitive neuroectodermal tumor, angiosarcoma; neoplasms of the hematopoietic system: myelodysplastic sydromes, acute myeloid leukemia, chronic myeloid leukemia, acute lymphocytic leukemia, HTLV-1 and T-cell leukemia/lymphoma, chronic lymphocytic leukemia, hairy cell leukemia, Hodgkin's disease, non-Hodgkin's lymphomas, mast cell leukemia; and neoplasms of children: acute lymphoblastic leukemia, acute myelocytic leukemias, neuroblastoma, bone tumors, rhabdomyosarcoma, lymphomas, renal tumors. In particular, the present compounds are believed to be useful in treating solid tumors, especially tumors of the colon and rectum. It is preferred that the mammal to be treated by the administration of the compounds of Formula I is human.

The compounds of the present invention are acidic in nature and accordingly may react with any of a number of inorganic and organic bases, for example, amines and quaternary ammonium bases, to form pharmaceutically acceptable base addition salts. It is preferable to convert the compounds of Formula I to their pharmaceutically acceptable base addition salts for ease of administration when aqueous solutions of the subject compound are required. The Formula I compounds can react with basic materials such as alkali metal- or alkaline earth metal hydroxides, carbonates, and bicarbonates including, without limitation, sodium hydroxide, sodium carbonate, potassium hydroxide, calcium hydroxide, and lithium hydroxide to form pharmaceutically acceptable salts such as the corresponding sodium, potassium, lithium, or calcium salt. The sodium and potassium salts are especially preferred.

Examples of amines suitable for forming salts are: primary, secondary and tertiary aliphatic and aromatic amines, such as methylamine, ethylamine, propylamine, i-propylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, especially ethyl-, propyl-, diethyl- or triethylamine, but particulary isopropylamine and diethanolamine.

Examples of quaternary ammonium bases are in general the cations of hydroxyammonium salts, for example the tetramethylammonium cation, the trimethylbenzylammonium cation, the triethylbenzylammonium cation, the tetraethylammonium cation or the trimethylethylammonium cation, but also the ammonium cation.

The skilled artisan will appreciate that the introduction of certain substituents will create asymmetry in the compounds of Formula I. The present invention contemplates all enantiomers and mixtures of enantiomers, including racemates. It is preferred that the compounds of the invention containing chiral centers are single enantiomers. The present invention further contemplates all diastereomers.

The compounds of the present invention can be prepared by a variety of procedures, some of which are illustrated in the schemes below. It will be recognized by one of skill in the art that the individual steps in the following schemes may be varied to provide the compounds of Formula I. Some of these variations are discussed.

The particular order of steps required to produce the compounds of Formula I is dependent upon the particular compound being synthesized, the starting compound, and the relative lability of the substituted moieties.

The compounds of the present invention may be prepared by methods well known to one of ordinary skill in the art. Generally, the compounds of Formula I can be prepared by coupling an appropriately substituted thienyl- or thiazolyl-sulfonamide with an appropriately substituted benzoic acid as illustrated in the following schemes. The variables $R^1$, $R^2$, X, and Y are as previously defined.

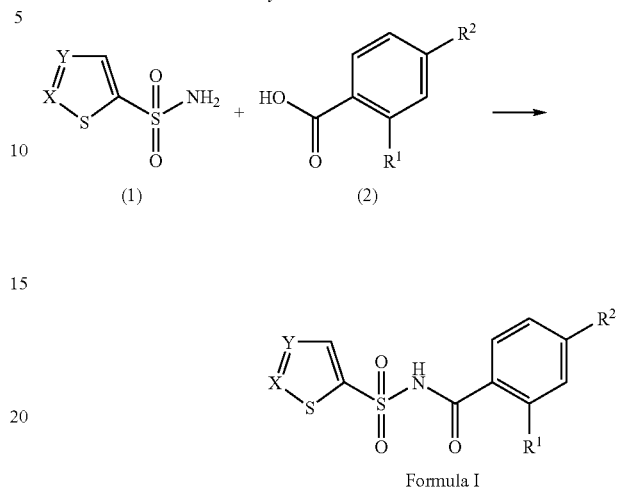

Synthetic Scheme I

The optionally substituted benzoic acid is coupled to an appropriate sulfonamide under standard peptide coupling conditions well known to the skilled artisan. Specifically, the thienyl- or the thiazolyl-sulfonamides and the benzoic acid are coupled in the presence of a peptide coupling reagent, optionally in the presence of a catalyst. Suitable peptide coupling reagents include N,N'-carbonyldiimidazole (CDI), N,N'-dicyclohexylcarbodiimide (DCC), 1-(3-dimethylaminopropyl)-3-ethylcarbodiimide hydrochloride (EDC), and 1-(3-(1-pyrrolidinyl)propyl)-3-ethylcarbodiimide (PEPC). Polymer supported forms of EDC (*Tetrahedron Letters*, 34(48), 7685 (1993)) and PEPC (U.S. Pat. No. 5,792,763) have been described, and are very useful for the preparation of the compounds of the present invention. Suitable catalysts for the coupling reaction include N,N-[dimethyl]-4-aminopyridine (DMAP). All of the reagents are combined in a suitable solvent, typically dichloromethane, chloroform, tetrahydrofuran, dioxane, or diethyl ether and are stirred for from 1 to 72 hours at a temperature of from ambient to about the reflux temperature of the solvent. Where excess or unreacted sulfonamide or benzoic acid remains in the reaction mixture, it may be removed by the addition of an appropriate acidic or basic resin, followed by filtration. Alternatively, these reagents may be removed by extractive techniques. The desired product may be isolated by standard extractive and crystallization techniques, and purified by chromatography or crystallization as necessary or desired. Where polymer-bound reagents are employed, they may be conveniently removed from the reaction mixture by filtration.

The requisite benzoic acids and sulfonamides are either commercially available or may be prepared by methods well known to the skilled artisan, such as in the following synthetic schemes. The variables $R^1$, $R^2$, X, and Y are as previously defined and Z is a cyano group or a halide.

Synthetic Scheme II

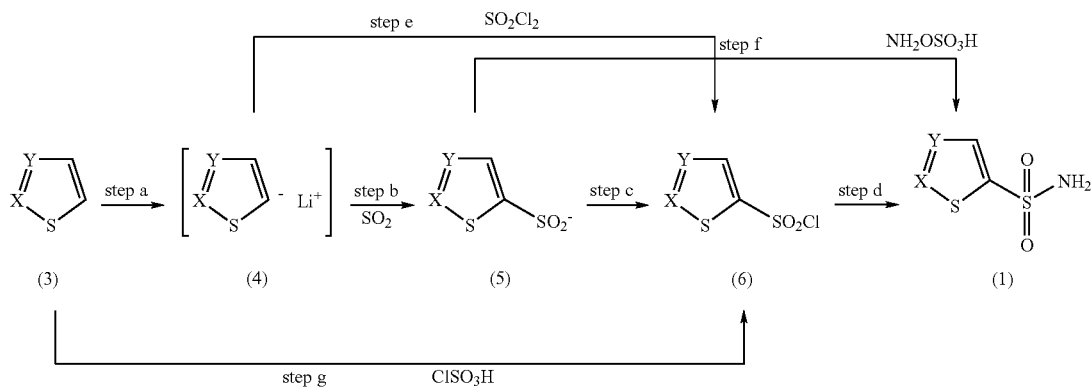

Synthetic Scheme II depicts sulfonylation of the thiophenes and thiazoles of formula (3) in the formation of the sulfonamides of formula (1). Synthetic conditions for sulfonylations are dependent on the functional groups of the thiophene starting material. For example, in (step a), a lithium base such as n-butyl lithium is used to create the anion of formula (4) in situ, at a temperature range of −78° C. to room temperature. The anion is quenched with a sulfonating reagent, such as sulfur dioxide, (step b) to give compounds of formula (5). Formula (5) can be further reacted with N-chlorosuccinimide, (step c), to afford sulfonyl chlorides of formula (6). Alternatively, formula (4) may be treated with sulfuryl chloride, (step e) to give the sulfonyl chlorides of formula (6) directly (Howbert, J. J.; Mohamadi, F.; Spees, M. M. European Patent 0 467 613 A1). The skilled artisan will also appreciate that the sulfonyl chloride of formula (6) may be prepared by the reaction of formula (3) with chlorosulfonic acid (step g). The sulfonyl chlorides of formula (6) can be contacted with ammonium hydroxide, (step d), to give the sulfonamides of formula (1)(Cremlyn, R. J.; Bassin, J. P. Farouk, S.; Potterton, M.; Mattu, T. *Phosphorus, Sulfur Silicon Relat. Elem.* 1992, 73 (1-4), 107-120); Besterman, J. M.; Delorme, D.; Rahil, J. WO 01 02411, 2001). Alternatively, formula (5) can be treated with hydroxylamine-O-sulfonic acid, (step f), to give sulfonamides of formula (1) directly (Mohamadi, F.; Spees, M. M. U.S. Pat. No. 5,169,860).

The synthetic conditions of Synthetic Scheme II are well known and appreciated in the art (J. Med. Chem., Graham, S. L., et al., 1989, 32, 2548-2554; J. Med. Chem., Barnish, I. T. et al., 1981, 24, 959; J. Chem. Soc., Cymerman-Craig, J., et al., 1956, 4115).

Synthetic Scheme III

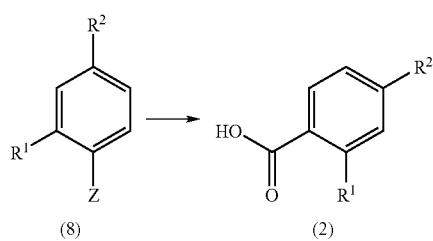

The preparation of the requisite benzoic acids (2) may be accomplished by functional transformations well known to the skilled artisan as illustrated in Synthetic Scheme III. For example, when Z is a cyano group the conversion to the carboxylic acid can be achieved under acidic conditions (Larock, R. C., *Comprehensive Organic Transformations*, 2$^{nd}$ Ed., copyright 1999, John Wiley & Sons, pp 1986-1987). When Z is a halide a metal promoted carbonylation can be performed with palladium acetate and carbon monoxide in methanol to give the methyl benzoate (Id. at 1685-1687), then followed by a hydrolysis to afford the benzoic acids of formula (2) (Id. at 1959-1968). One skilled in the art will appreciate further manipulation of the R groups of the starting compounds of formula (3) and (8) that are done by known synthetic interconversions such as an amino derivative to the corresponding halide (Id. at 677-679), a halide exchange with a metal-alkoxide (Id. at 893-894) or a nucleophilic addition of appropriate sulfur or nitrogen nucleophiles (Id. at 779-780).

The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired. Furthermore, the skilled artisan will appreciate that in many circumstances, the order in which moieties are introduced is not critical.

The following preparations and examples further illustrate the preparation of compounds of the present invention and should not be interpreted in any way as to limit the scope. Those skilled in the art will recognize that various modifications may be made while not departing from the spirit and scope of the invention. All publications mentioned in the specification are indicative of the level of those skilled in the art to which this invention pertains.

The terms and abbreviations used in the instant Preparations and Examples have their normal meanings unless otherwise designated. For example "° C.", "N", "mmol", "g", "mL", "M", "HPLC", "IR", "MS(FD)", "MS(IS)", "MS(FIA)", "MS(FAB)", "MS(EI)", "MS(ES)", "UV", "TLC" and "$^{1}$H NMR", refer to degrees Celsius, normal or normality, millimole or millimoles, gram or grams, milliliter or milliliters, molar or molarity, high performance liquid chromatography, infra red spectrometry, field desorption mass spectrometry, ion spray mass spectrometry, flow injection analysis mass spectrometry, fast atom bombardment mass spectrometry, electron impact mass spectrometry, electron spray mass spectrometry, ultraviolet spectrometry, thin layer chromatography and proton nuclear magnetic resonance spectrometry respectively. In addition, the absorption maxima listed for the IR spectra are only those of interest and not all of the maxima observed.

Preparation 1

5-(Methylthio)thiophene-2-sulfonamide

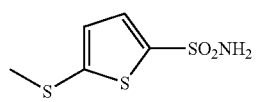

1.3 M n-Butyllithium in tetrahydrofuran (10 mL, 12.5 mmol; Aldrich) is added to a cold solution (−78° C.) of the 2-(methylthio)thiophene (10.0 mmol; Aldrich) in anhydrous tetrahydrofuran (5.0 mL/mmol). The mixture is allowed to react for 90 min under nitrogen atmosphere. Sulfur dioxide is bubbled through the solution for 30 min at −78° C. The mixture is warmed to room temperature and concentrated by rotary evaporation. The residue is treated with a solution of sodium acetate (8 eq.) and hydroxylamine-O-sulfonic acid (2.5 eq) in water (4 mL/mol) and stirred at 25° C. for 1 hr. The reaction mixture is made basic by addition of 1.0 N sodium hydroxide to pH 10 and is extracted with diethyl ether (2×50 mL). The aqueous phase is acidified to pH 2 with conc. hydrochloric acid and extracted with methylene chloride (2×50 mL). The combined organic phases are washed with saturated sodium bicarbonate (3×25 mL) and brine (50 mL), dried (sodium sulfate), filtered, and concentrated by rotary evaporation. The crude solid is purified by column chromatography with a mixture hexane/ethyl acetate (2:1) as the eluent. $^1$H NMR (300 MHz), CDCl$_3$) δ: 7.52 (d, 1H), 6.94 (d, 1H), 5.10 (br s, 2H), 2.58 (s, 3H).

Preparation 2

5-(Ethyl)thiophene-2-sulfonamide

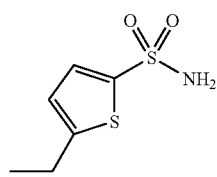

A solution of 2-ethylthiophene (1.78 mmol) dissolved in chloroform (1 mL/mmol) is added to a cold solution (0° C.) of chlorosulfonic acid (0.35 mL, 5.35 mmol) in chloroform (1.3 mL/mmol). The mixture is stirred for 3 hr at room temperature with a drying tube connected.

The mixture is then poured over a cold mixture of chloroform/water and stirred 10 min. The organic layer is washed with water, dried over sodium sulfate and concentrated in vacuo. Two mL of an aqueous solution of ammonium hydroxide is added to the crude oil and the mixture is stirred for 30 min. Solvent is concentrated in vacuo. The residue is employed without further purification. $^1$H NMR (200 MHz, CDCl$_3$) δ: 7.48 (d, 1H, J=3.6 Hz), 6.74 (dd, 1H, J=3.7 Hz, 0.8 Hz), 5.2 (br s, 2H), 2.9 (q, 2H, J=7.5 Hz), 1.32 (t, 3H, J=7.5 Hz).

Preparation 3

5-(Propyl)thiophene-2-sulfonamide

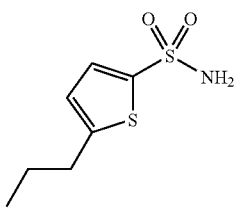

A method similar to PREPARATION 2, with an exception for 2-n-propylthiophene, is used. $^1$H NMR (200 MHz, CDCl$_3$) δ: 7.46 (d, 1H, J=3.8 Hz), 6.72 (dd, 1H, J=3.8 Hz, 0.8 Hz), 5.30 (bs, 2H), 2.79 (t, 2H, J=7.4 Hz), 1.69 (q, 2H, J=7.4 Hz), 0.97 (t, 3H, J=7.4 Hz).

Preparation 4

5-(Methoxy)thiophene-2-sulfonamide

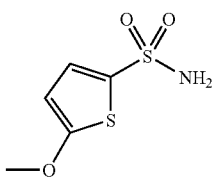

1.6 M n-butyllithium (1 mL, 1.75 mmol) is added to a cold solution (−78° C.) of 2-methoxythiophene (1.75 mmol) in anhydrous tetrahydrofuran (2.6 mL/mmol). The mixture is allowed to react for 45 min under a nitrogen atmosphere. The solution is then warmed to 0° C. and sulfur dioxide is bubbled through the solution for 15 min and then the mixture is purged with nitrogen. The solvent is removed in vacuo and the crude oil is dissolved in anhydrous methylene chloride (1 mL/mmol) and N-chlorosuccinimide is added (1.75 mmol). The mixture is stirred for 2 hr at room temperature under a nitrogen atmosphere. It is filtered and then concentrated in vacuo. The crude oil is dissolved in acetone (3 mL/mmol) and 2 mL of an aqueous solution of ammonium hydroxide is added. The solution is stirred overnight. The solvent is concentrated in vacuo. The residue is dissolved in ethyl acetate and washed with water and brine, dried over sodium sulfate, and concentrated under vacuum. The residue is purified by column chromatography with a mixture hexane/ethyl acetate (7:3) as the eluent. $^1$H NMR (200 MHz, CDCl$_3$) δ: 7.37 (d, 1H, J=4.3 Hz), 6.17 (d, 1H, J=4.3 Hz), 4.9 (br s, 2H), 3.94 (s, 3H).

Preparation 5

5-(Methyl)thiophene-2-sulfonamide

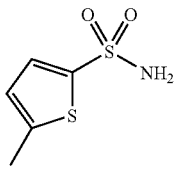

A method similar to PREPARATION 2, with an exception for 2-(methyl)thiophene, is used. $^1$H NMR (200 MHz, CDCl$_3$) δ: 7.44 (d, 1H, J=3.7 Hz), 6.71 (br d, 1H, J=3.7 Hz), 4.92 (br s, 2H), 2.51 (d, 3H, J=0.9 Hz).

Preparation 6

5-(Methoxymethyl)thiophene-2-sulfonamide

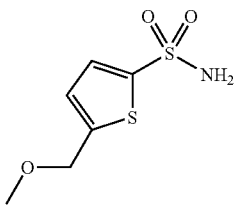

2-(Hydroxymethyl)thiophene (4.4 mmol; Aldrich), silver (I) oxide (6.6 mmol, 1.5 eq; Aldrich) and methyl iodide (2.2 mmol, 5 eq; Aldrich) are dissolved in methylene chloride (2 mL/mmol) and stirred at room temperature for 48 hr. The mixture is filtered through celite and the solvent is evaporated in vacuo. The residue is purified by column chromatography with a mixture hexane/ethyl acetate (75:25) as the eluent.

1.6 M N-butyllithium in tetrahydrofuran (0.6 mL, 0.9 mmol; Aldrich) is added to a cold solution (−78° C.) of the above product, 2-(methoxymethyl)thiophene (0.87 mmol) in anhydrous tetrahydrofuran (1.3 mL/mmol). The mixture is allowed to react for 30 min under a nitrogen atmosphere and is transferred via canula over a solution of sulfuryl chloride (0.1 mL, 1.7 mmol; Aldrich) in hexane (2.5 mL/mmol). The solution is stirred under a nitrogen atmosphere for 2 hr and warmed to room temperature. The mixture is diluted with ethyl acetate and washed with water and brine, dried over sodium sulfate, and concentrated in vacuo. The residue is dissolved in acetone (3 mL/mmol) and 2 mL of an aqueous solution of ammonium hydroxide is added with the solution stirred overnight. The solvent is concentrated in vacuo. The residue is dissolved in ethyl acetate and washed with water and brine, dried over sodium sulfate, and concentrated under vacuum. The residue is purified by column chromatography with a mixture hexane/ethyl acetate (7:3) as the eluent. $^1$H NMR (200 MHz, CDCl$_3$) δ: 7.52 (d, 1H, J=3.7 Hz), 6.92 (d, 1H, J=3.7 Hz), 5.23 (br s, 2H), 4.60 (s, 2H), 3.41 (s, 3H).

Preparation 7

4,5-Dibromothiophene-2-sulfonamide

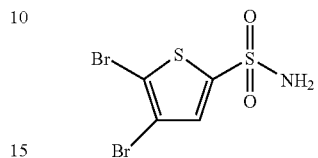

Phosphorus pentachloride (0.16 g, 0.8 mmol) is added portionwise with stirring to chlorosulfonic acid (0.14 g, 1.2 mmol) and the resultant solution is cooled to 0° C., under a nitrogen atmosphere. 2,3-Dibromothiophene (0.24 g, 0.8 mmol) is added with stirring and the resultant mixture is heated to 50° C. for 1 hr. Ice-water is added to the reaction mixture and then it is extracted with ethyl acetate (20 mL). The organic layer is concentrated and re-dissolved in acetone (5 mL). Ammonium hydroxide (5 mL, concentrated) is added and the resulting mixture stirred for 30 min at room temperature. Brine (10 mL) and ethyl acetate (20 mL) are added, the organic layer is separated, and the aqueous layer is extracted one more time with ethyl acetate (10 mL). The combined organic layers are dried over sodium sulfate, concentrated in vacuo, and then chromatographed on silica (0.5% methyl alcohol in methylene chloride) to give the title compound (58% yield) as a brown solid. ES(−)MS m/z 318, (M−H)$^-$ consistent with 2 Br.

Preparation 8

5-(Cyano)thiophene-2-sulfonamide

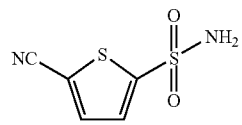

A mixture of 5-bromothiophene-2-sulfonamide (0.50 g, 2.1 mmol), zinc cyanide (0.25 g, 2.1 mmol), tetrakis(triphenylphosphine)palladium(0) (0.072 g, 0.06 mmol) in dimethylformamide (5 mL, anhydrous) is placed under microwave radiation (under nitrogen atmosphere, 160° C.) for 15 min. Thin layer chromatography (5% methyl alcohol in methylene chloride) demonstrates the reaction is incomplete. Additional tetrakis-(triphenylphosphine)palladium(0) (0.24 g, 0.2 mmol) and dimethylformamide (10 mL) are added to the reaction mixture and placed under microwave radiation (under nitrogen atmosphere at 160° C.) for 37 min. 10 mL of water and 20 mL of ethyl acetate are added to the reaction mixture. The organic phase is separated and the aqueous layer is extracted with 20 mL ethyl acetate. The combined organic layers are dried over sodium sulfate, concentrated in vacuo, and then chromatographed on silica (0-5% methyl alcohol in methylene chloride) to give the title compound, as a white solid (0.22 g, 57% yield).

ES(−)MS m/z 187, (M−H)$^-$.

Preparation 9

5-(Methoxycarbonyl)thiophene-2-sulfonamide

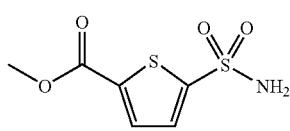

A mixture of 5-bromothiophene-2-sulfonamide (0.50 g, 2.1 mmol), triethyl amine (1 mL), methanol (1 mL), palladium acetate (0.046 g, 2.1 mmol) and 1,3-bis(diphenylphosphino) propane (0.085 g, 2.1 mmol) (addition in that order) in dimethylformamide (5 mL, anhydrous) is saturated with carbon monoxide gas, at room temperature. This reaction mixture is heated to 100° C. and stirred overnight, under a carbon monoxide atmosphere. 10 mL of brine and 10 mL of ethyl acetate are added to the reaction mixture. The organic phase is separated and the aqueous layer is extracted with 10 mL ethyl acetate. The combined organic layers are dried over sodium sulfate, concentrated in vacuo, and then chromatographed on silica (0-1% methyl alcohol in methylene chloride) to give the title compound, as a yellow solid (0.15 g, 34% yield).

ES(−)MS m/z 220, (M−H)−.

Preparation 10

2-Chlorothiazole-5-sulfonamide

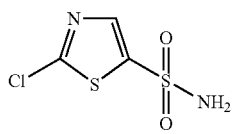

A method similar to PREPARATION 4, with an exception for 2-chlorothiazole, is used.

Preparation 11

2-Methoxythiazole-5-sulfonamide

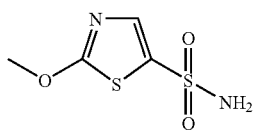

A method similar to PREPARATION 1, with an exception for 2-methoxy-thiazole, is used.

Preparation 12

2-Isopropyl-2,5-dihydrothiazole

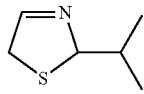

A solution of 1,4-dithiane-2,5-diol (20 g, 131 mmol) is suspended in $Et_2O$ (80 mL) in a round bottom flask that is equipped with a condenser and a gas inlet tube. Isobutyraldehyde (40 mL) and $Na_2SO_4$ (12 g) are added then ammonia is bubbled through the reaction mixture for 20 min at room temperature and 10 min at reflux. The reaction is then cooled to room temperature and the $Na_2SO_4$ is filtered and the solvent is distilled at atmospheric pressure. The residue is distilled via a vigreaux column at 130° C. at 7 in/Hg to afford the title compound (13.4 g, 40%).

ES(+)MS m/z 130, (M+H)+.

Preparation 13

2-Isopropylthiazole

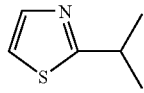

A solution of 2-isopropyl-2,5-dihydrothiazole (12.4 g, 95.9 mmol) in benzene (125 mL) is added to a solution of p-chloranil (23.6 g, 95.6 mmol). The reaction mixture is refluxed for 2 hr and cooled to room temperature. A solution of 2 M NaOH (200 mL) is added and the reaction is stirred for 5 min then poured into a separatory funnel. The organic layer is separated and washed with 2 M NaOH (200 mL) and $H_2O$ (2×100 mL). The aqueous layers are re-extracted with benzene and the organic layers are combined. Benzene is distilled off at atmospheric pressure to leave an oily residue which is distilled via a vigreaux column at 110° C. at 8 in/Hg to provide the title compound (6.13 g, 48%) as a colorless oil.

ES(+)MS m/z 128, (M+H)+.

Preparation 14

2-Isopropylthiazole-5-sulfonamide

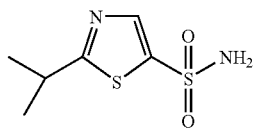

To a solution of 2-isopropylthiazole (2 g, 15.7 mmol) in $Et_2O$ (75 mL) at −78° C. is added n-BuLi (12.8 mL of 1.6 M in hexanes, 20.4 mmol) dropwise (a pink precipitate is observed). After 40 min, the reaction mixture is warmed to 0° C. for 10 min then re-cooled to −78° C. Sulfur dioxide is bubbled over the surface of the reaction mixture for 5 min.

The reaction mixture is warmed to room temperature and stirred for an additional 2.5 hr. The reaction is cooled to 0° C. and N-chlorosuccinimide (4.20 g, 32.4 mmol) is added and the reaction is stirred for 1.5 hr. The reaction mixture is then filtered and the precipitate is washed with Et₂O. The filtrate is concentrated under vacuum to give crude sulfonyl chloride which is dissolved in acetone (20 mL) and added to a stirred solution of concentrated NH₄OH (20 mL) in acetone (50 mL) at 0° C. The reaction mixture is stirred for 5 min and then partitioned between EtOAc and H₂O. The aqueous layer is separated and extracted with EtOAc (2×). The organic layers are combined, dried (MgSO₄), filtered and evaporated under reduced pressure. The crude product is recrystallized from CH₂Cl₂/acetone/hexanes to afford the title compound (1.89 g, 58%).

ES(+)MS m/z 207, (M+H)⁺.

Preparation 15

2-Methylthiazole

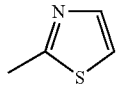

To a stirred solution of 2-bromothiazole (5.0 g, 30.5 mmol) in Et₂O (60 mL) at −78° C. under nitrogen is added dropwise n-BuLi (14.6 mL of 1.6 M in hexanes, 36.6 mmol). The reaction mixture is stirred for 40 min then dimethyl sulfate (4.75 mL, 50.3 mmol) is added dropwise and the reaction mixture is warmed to −10° C. (placed in a refrigerator) and left standing overnight. The reaction is warmed to 0° C. and cautiously quenched with 2 M HCl (40 mL). The organic layer is separated and extracted with 2 M HCl (2×). The acid extracts are combined and made strongly alkaline with 2 M NaOH and extracted with Et₂O (4×). The combined organic extracts are dried over KOH and the solvent is distilled off at atmospheric pressure then the title compound is distilled off at 128-130° C. (1.5 g, 49%).

ES(+)MS m/z 100, (M+H)⁺.

Preparation 16

2-Methylthiazole-5-sulfonamide

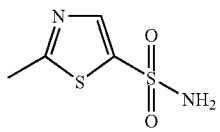

To a stirred solution of n-BuLi (12.1 mL of 1.6 M in hexanes, 19.4 mmol) in Et₂O (70 mL) at −78° C. under nitrogen is added dropwise a solution of 2-methyl-thiazole (1.48 g, 14.9 mmol) in Et₂O (70 mL). The reaction mixture is stirred at −78° C. for 40 min then warmed to −20° C. Sulfur dioxide is bubbled over the solution for 5 min then the reaction is allowed to warm to room temperature overnight. N-Chlorosuccinimide (3.99 g, 29.9 mmol) is added and the reaction mixture allowed to stir for 1 hr. The reaction is filtered and the filtrate concentrated under vacuum to provide the crude product. The crude product is dissolved in acetone (30 mL) and concentrated NH₄OH (20 mL) is added and the mixture stirred for 15 min. The reaction mixture is partitioned between EtOAc and H₂O. The aqueous layer is extracted with EtOAc (2×) and the organic layers are combined, dried (MgSO₄), filtered and concentrated under vacuum. Flash chromatography on silica gel eluting with a gradient [Hex to Hex:EtOAc (1:1)] provides the title compound (282 mg, 11%) as a tan solid.

ES(−)MS m/z 177, [M−H]⁻.

Preparation 17

2-Bromo-3-chlorothiophene

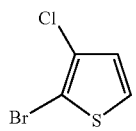

To a solution 3-chlorothiophene (5.0 g, 42 mmol) in a mixture of CHCl₃ (50 mL) and AcOH (50 mL) is added N-bromosuccinimide (8.3 g, 46 mmol). The solution is heated to 50° C. After 1.5 hr, the reaction mixture is cooled to room temperature. Brine (100 mL) and Et₂O (200 mL) are added to the reaction mixture and the aqueous layer is extracted with Et₂O (100 mL). The combined organic extracts are washed with saturated NaHCO₃ then dried (Na₂SO₄), filtered and concentrated in vacuo to afford the title compound (5.4 g, 65%).

¹H NMR (300 MHz, CD₃OD) δ 6.94 (d, J=5.8 Hz, 1H), 7.50 (d, J=5.8 Hz, 1H)

Preparation 18

5-Bromo-4-chlorothiophene-2-sulfonamide

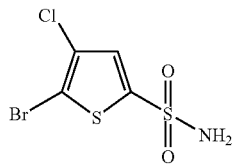

To phosphorous pentachloride (4.6 g, 22.2 mmol) is added chlorosulfonic acid (2.2 mL, 33.3 mmol) under a nitrogen atmosphere. The solution is cooled to 0° C. and 2-bromo-3-chlorothiophene (1.0 g, 5.0 mmol) is added. The mixture is heated to 50° C. for 1 hr. The reaction is cooled then quenched with ice/water and the solution is extracted with CH₂Cl₂ (200 mL), and then the CH₂Cl₂ is removed under reduced pressure. The residue is dissolved in acetone (30 mL) and added to a solution of 29% NH₄OH (40 mL) in acetone (100 mL) at 0° C. The reaction mixture is stirred for 0.5 hr then the acetone is removed under reduced pressure. The residue is extracted with EtOAc (200 mL). The organic layer is washed with brine then dried (Na₂SO₄), filtered and concentrated in vacuo to afford the title compound (8.1 g, >100%), which is used without further purification.

ES(−)MS m/z 274, [M−H]⁻ consistent with 1 Br and 1 Cl.

Preparation 19

4-Chlorothiophene-2-sulfonamide

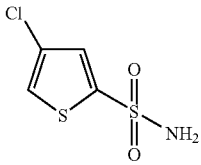

To a stirred solution of 5-bromo-4-chlorothiophene-2-sulfonamide (2.4 g, 8.7 mmol) in AcOH (20 mL) is added zinc dust (1.7 g, 26.0 mmol). The reaction mixture is heated to 120° C. for 6 hr. After 6 hr, the mixture is filtered and neutralized with 1 M NaOH. The aqueous layer is extracted with EtOAc (2×100 mL). The combined organic extracts are dried (Na$_2$SO$_4$), filtered and concentrated in vacuo. The crude product is chromatographed on silica gel, eluting with CH$_2$Cl$_2$ to afford the title compound (0.88 g, 52%).

$^1$H NMR (300 MHz, CD$_3$OD) δ 7.48 (s, 1H), 7.58 (s, 1H)

Preparation 20

2-Bromo-3-methylthiophene

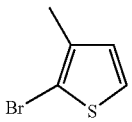

3-Methylthiophene (5.0 g, 50.9 mmol) is dissolved in a solution of CHCl$_3$ (50 mL) and AcOH (50 mL). N-Bromosuccinimide (9.5 g, 53.5 mmol) is added to the solution and the mixture is heated to 50° C. After 1.5 hr, the reaction mixture is cooled to room temperature. Brine (100 mL) and Et$_2$O (200 mL) are added to the reaction mixture. The organic layer is separated and washed with 1 M NaOH and brine then dried (Na$_2$SO$_4$), filtered and concentrated in vacuo to give the title compound (6.4 g, 71%) as a clear oil.

$^1$H NMR 300 MHz (CD$_3$OD) δ 2.14 (s, 3H), 6.81 (d, J=5.6 Hz, 1H), 7.28 (d, J=5.6 Hz, 1H)

Preparation 21

5-Bromo-4-methylthiophene-2-sulfonamide

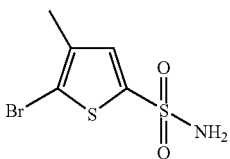

To phosphorous pentachloride (6.5 g, 31 mmol) is added chlorosulfonic acid (3.1 mL, 46.4 mmol). The mixture is cooled to 0° C. and 2-bromo-3-methylthiophene (5.4 g, 31 mmol) is added. The reaction mixture is heated to 50° C. for 1 hr. The reaction is cooled/quenched with ice/water and the solution extracted with CH$_2$Cl$_2$ (200 mL). The organic layer is washed with brine, dried (Na$_2$SO$_4$), filtered and concentrated in vacuo. The residue is dissolved in acetone (20 mL) and added to a solution of 29% NH$_4$OH (54 mL) in acetone (250 mL). The reaction mixture is stirred for 0.5 hr then the acetone is removed under reduced pressure. The residue is extracted with EtOAc (2×100 mL). The combined organic extracts are washed with brine, dried (Na$_2$SO$_4$), filtered and concentrated in vacuo. The crude product is chromatographed on silica gel, eluting with CH$_2$Cl$_2$ to afford the title compound (5.3 g, 58%).

$^1$H NMR (300 MHz, CD$_3$OD) δ 2.20 (s, 3H), 7.32 (s, 1H)

Preparation 22

4-Methylthiophene-2-sulfonamide

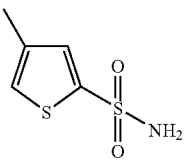

To a stirred solution of 5-bromo-4-methylthiophene-2-sulfonamide (3.1 g, 12.1 mmol) in AcOH (30 mL) is added zinc dust (2.4 g, 36.2 mmol). The reaction mixture is heated to reflux for 8 hr. After 8 hr, the reaction mixture is cooled and filtered. The filtrate is neutralized with 1 M NaOH. The aqueous layer is extracted with EtOAc (300 mL). The organics are dried (Na$_2$SO$_4$), filtered and concentrated in vacuo. The crude product is chromatographed on silica gel, eluting with CH$_2$Cl$_2$ to afford the title compound (0.90 g, 43%).

$^1$H NMR (300 MHz, CD$_3$OD) δ 2.26 (s, 3H), 7.27 (s, 1H), 7.41 (s, 1H)

Preparation 23

2-Trimethylsilyl-3-methoxythiophene

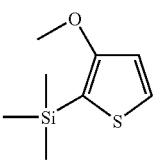

A solution of n-BuLi (19.7 mL of 1.6 M in hexanes, 31.5 mmol) is added dropwise to a solution of 3-methoxythiophene (3.0 g, 26.3 mmol) in anhydrous Et$_2$O (20 mL) under nitrogen at −70° C. The mixture is stirred at −70° C. for 2 hr. Chlorotrimethylsilane (4.5 mL, 35.4 mmol) is added slowly to the solution. The mixture is warmed to room temperature and stirred for 3 hr. The reaction is quenched with water (50 mL) and hexanes (100 mL). The aqueous layer is extracted with hexanes (50 mL). The combined organic extracts are dried (Na$_2$SO$_4$), filtered and concentrated. The crude product is chromatographed on silica gel, eluting with hexanes to afford the title compound (4.0 g, 82%) as a colorless liquid.

¹H NMR 300 MHz (CD₃OD) δ 0.29 (s, 9H), 3.81 (s, 3H), 6.92 (d, J=4.9 Hz, 1H), 7.40 (d, J=4.9 Hz, 1H)

Preparation 24

5-Trimethylsilyl-4-methoxythiophene-2-sulfonamide

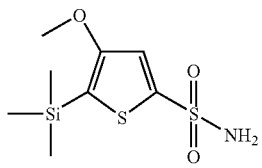

A solution of n-BuLi (11.8 mL of 2.5 M in hexanes, 29.4 mmol) is added dropwise to a solution of 2-trimethylsilyl-3-methoxythiophene (2.19 g, 11.8 mmol) in anhydrous THF (40 mL) under nitrogen at −70° C. The mixture is stirred at −70° C. for 4 hr then sulfur dioxide is bubbled through the solution for 5 minutes. After stirring 2.5 hr, N-chlorosuccinimide (3.15 g, 23.6 mmol) is added to the suspension. The mixture is warmed to room temperature and stirred for 1 hr then the reaction mixture is filtered and the solids are washed with CH₂Cl₂. The filtrate is concentrated and the residue is dissolved in CH₂Cl₂ (200 mL). The organic layer is washed with brine then dried (Na₂SO₄), filtered and concentrated. The residue is dissolved in acetone (20 mL) and added to a solution of 29% NH₄OH (20 mL) in acetone (30 mL) at 0° C. The mixture is stirred at 0° C. for 30 min then the acetone is removed under reduced pressure and the residue is extracted with EtOAc (2×100 mL). The organic extracts are washed with brine then dried (Na₂SO₄), filtered and concentrated. The crude product is chromatographed on silica gel, eluting with Hex:EtOAc (3:1) to afford the title compound (0.77 g, 25%).

¹H NMR 300 MHz (CD₃OD) δ 0.29 (s, 9H), 3.31 (s, 3H), 7.49 (s, 1H)

Preparation 25

4-Methoxythiophene-2-sulfonamide

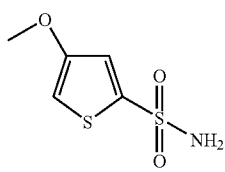

To a solution of 5-trimethylsilyl-4-methoxythiophene-2-sulfonamide (770 mg, 2.90 mmol) in THF (10 mL) is added a solution of tetra-butylammonium fluoride (17.4 mL of 1 M in THF, 17.4 mmol). The reaction mixture is stirred at room temperature for 2 hr. The THF is removed under reduced pressure. The residue is dissolved in EtOAc (200 mL). The organic layer is washed with brine then dried (Na₂SO₄), filtered and concentrated in vacuo. The crude product is chromatographed on silica gel, eluting with Hex:EtOAc (3:1) to afford the title compound (480 mg, 86%).

¹H NMR (300 MHz, CD₃OD) δ 3.81 (s, 3H), 6.73 (s, 1H), 7.22 (s, 1H)

Preparation 26

5-Bromo-4-methoxythiophene-2-sulfonamide

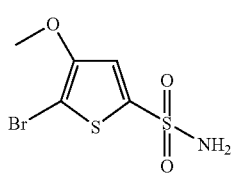

To a solution of 4-methoxythiophene-2-sulfonamide (240 mg, 1.24 mmol) in CH₂Cl₂ (40 mL) is added N-bromosuccinimide (287 mg, 1.61 mmol). The reaction mixture is stirred at 0° C. for 7 hr. After 7 hr, the reaction mixture is diluted with CH₂Cl₂ (150 mL). The organic layer is washed with brine then dried (Na₂SO₄), filtered and concentrated in vacuo. The crude product is chromatographed on silica gel, eluting with Hex:EtOAc (2:1) to afford the title compound (277 mg, 82%).

¹H NMR (300 MHz, CD₃OD) δ 3.30 (s, 3H), 7.40 (s, 1H)

Preparation 27

2-Trimethylsilyl-3-methylsulfanylthiophene

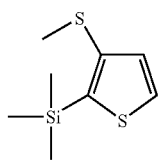

A solution of n-BuLi (5.3 mL of 1.6 M in hexanes, 8.5 mmol) is added dropwise to a solution of 3-methylsulfanylthiophene (1.0 g, 7.7 mmol) in anhydrous Et₂O (8 mL) under nitrogen at −70° C. The mixture is stirred at −70° C. for 2 hr. Chlorotrimethylsilane (1.5 mL) is added slowly to the reaction mixture. The mixture is warmed to room temperature and stirred for 3 hr. The reaction is quenched with water (50 mL) and Et₂O (50 mL). The aqueous layer is extracted with Et₂O (50 mL). The combined organic extracts are dried (Na₂SO₄), filtered and concentrated. The crude product is chromatographed on silica gel, eluting with hexanes to afford the title compound (0.75 g, 48%) as a colorless liquid.

¹H NMR 300 MHz (CD₃OD) δ 0.38 (s, 9H), 2.42 (s, 3H), 7.17 (d, J=3.7 Hz, 1H), 7.51 (d, J=3.7 Hz, 1H)

Preparation 28

(5-Trimethylsilyl-4-methylsulfanylthiophene-2-sulfonamide

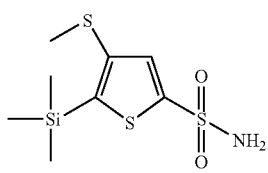

A solution of n-BuLi (7.4 mL of 2.5 M in hexanes, 18.4 mmol) is added dropwise to a solution of 2-trimethylsilyl-3-methylsulfanylthiophene (1.5 g, 7.4 mmol) in anhydrous THF (25 mL) under nitrogen at −70° C. The mixture is stirred at at −70° C. for 4 hr. Sulfur dioxide is bubbled through the solution at −70° C. for 5 minutes. After 2.5 hr, N-chlorosuccinimide (1.98 g, 14.8 mmol) is added to the suspension. The mixture is stirred at room temperature for 1 hr. The reaction mixture is filtered and solids washed with $CH_2Cl_2$. The filtrate is concentrated and the residue dissolved in $CH_2Cl_2$ (200 mL). The organic layer is washed with brine then dried ($Na_2SO_4$), filtered and concentrated. The residue is dissolved in acetone (20 mL) and added to a solution of 29% $NH_4OH$ (13 mL) in acetone (30 mL) at 0° C. The mixture is stirred at 0° C. for 30 min. The acetone is removed under reduced pressure and the residue is extracted with EtOAc (2×100 mL). The organic extracts are washed with brine then dried ($Na_2SO_4$), filtered and concentrated. The crude product is chromatographed on silica gel, eluting with Hex:EtOAc (3:1) to afford the title compound (0.65 g, 34%).

$^1$H NMR (300 MHz, $CD_3OD$) δ 0.39 (s, 9H), 2.45 (s, 3H), 7.65 (s, 1H)

Preparation 29

4-Methylsulfanylthiophene-2-sulfonamide

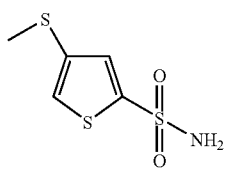

To a solution of 5-trimethylsilyl-4-methylsulfanylthiophene-2-sulfonamide (660 mg, 2.34 mmol) in THF (10 mL) is added a solution of tetra-butylammonium fluoride (14.0 mL of 1 M in THF, 14.0 mmol). The reaction mixture is stirred at room temperature for 3 hr. The THF is removed under reduced pressure and the residue is dissolved in EtOAc (200 mL). The organic layer is washed with brine then dried ($Na_2SO_4$), filtered and concentrated in vacuo. The crude product is chromatographed on silica gel, eluting with Hex:EtOAc (2:1) to afford the title compound (400 mg, 82%).

$^1$H NMR (300 MHz, $CD_3OD$) δ 2.49 (s, 3H), 7.35 (s, 1H), 7.47 (s, 1H)

Preparation 30

5-Bromo-4-methylsulfanylthiophene-2-sulfonamide

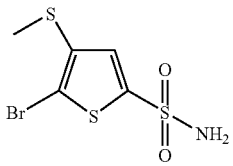

To a solution of 4-methylsulfanylthiophene-2-sulfonamide (210 mg, 1.00 mmol) in $CHCl_3$ (10 mL) and AcOH (10 mL) is added N-bromosuccinimide (231 mg, 1.30 mmol). The reaction mixture is stirred at room temperature for 7 hr. After 7 hr, the reaction mixture is neutralized with 1 M NaOH and the solution is extracted with EtOAc (200 mL). The organic layer is washed with brine then dried ($Na_2SO_4$), filtered and concentrated in vacuo. The crude product is chromatographed on silica gel, eluting with Hex:EtOAc (3:1) to afford the title compound (200 mg, 70%).

$^1$H NMR (300 MHz, $CD_3OD$) δ 2.49 (s, 3H), 7.45 (s, 1H)

Preparation 31

2,4-Dibromobenzonitrile

Copper cyanide (2.32 g, 25.9 mmol) is added to stirred anhydrous dimethylsulfoxide (50 mL) at 60° C. to form a clear solution, followed by the addition of tert-butylnitrite (7.1 mL, 59.7 mmol) all at once. A solution of 2,4-dibromoaniline 21 (5.0 g, 19.9 mmol) in anhydrous dimethylsulfoxide (30 mL) is added dropwise, via cannula, to the mixture. After the addition is complete, the reaction mixture is allowed to stir for 1 hr. After being cooled to 45° C., the mixture is slowly treated with 5N hydrochloric acid (50 mL). Five minutes later, the reaction mixture is cooled to ambient temperature before being extracted with ethyl acetate/hexane (1:1; 2×300 mL).

The combined organic layers are washed with water (100 mL) and brine (100 mL), dried, concentrated in vacuo, and then chromatographed on silica (0-5% ethyl acetate in hexane) to give the title compound (1.61 g, 31% yield). FD(+)MS m/z 259, ($M^+$) consistent with 2 Br.

Preparation 32

2,4-Dibromobenzoic acid

A stirred suspension of 2,4-dibromobenzonitrile (1.57 g, 6.0 mmol) in sulfuric acid (6 M, 150 mL) is heated to reflux for 3 days. The reaction mixture is cooled to ambient temperature before being extracted with ethyl acetate (2×75 mL). The combined organic layers are washed with water (100 mL) and brine (50 mL), dried, concentrated, and then chromatographed on silica (acetic acid/methyl alcohol/chloroform, 0.1:0.5:99.4) to give the title compound (0.81 g, 48% yield). mp 171-172° C.; ES(−)MS m/z 277, (M−H)$^-$ consistent with 2 Br.

Preparation 33

2-Bromo-4-chlorobenzoic acid

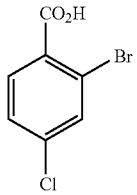

An aqueous solution of sodium nitrate (2.21 g) in water (15 mL) is added dropwise to a stirred, ice-cooled mixture of 2-amino-4-chlorobenzoic acid (5.00 g, 29.1 mmol) and 48% hydrobromic acid (150 mL) in water (150 mL). The resultant mixture is stirred for 2 hr at 0° C. Then it is treated dropwise with an aqueous solution of copper bromide (7.81 g) in water (20 mL). Upon the completion of the addition, the reaction mixture is allowed to warm to ambient temperature where it is stirred overnight. After extraction with ethyl acetate/hexanes (3:1; 2×400 mL), the combined organic layers are washed with brine (200 mL), dried, concentrated, and chromatographed on silica (1% methyl alcohol and 0.5% acetic acid in chloroform) to give the title compound (4.04 g, 59% yield). mp 154-155° C.; ES(−)MS m/z 233, (M−H)⁻ consistent with 1 Br and 1 Cl.

Preparation 34

2-Chloro-4-methylbenzoic acid

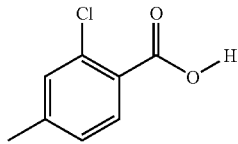

To 4-bromo-3-chlorotoluene (4.97 g, 24.2 mmol) in dimethylformamide (25 mL) is added palladium acetate (0.54 g, 2.42 mmol), 1,3-bis(diphenylphosphino)propane (0.998 g, 2.42 mmol), triethylamine (12.5 mL) and methanol (12.5 mL). The reaction vessel is evacuated and purged three times with carbon monoxide gas. A balloon filled with carbon monoxide gas is used to maintain the carbon monoxide atmosphere. The reaction mixture is heated at 80° C. for 8 hr. The mixture is washed with water and extracted with hexanes (2×50 mL). The combined organic layers are dried over sodium sulfate, filtered, concentrated, and chromatographed with 0-3% ethyl acetate in hexanes. 1.24 g (28%) of methyl 2-chloro-4-methylbenzoate is isolated as a colorless oil.

ES(+)MS m/z 184, (M+H)⁺ consistent with 1 Cl.

To methyl 2-chloro-4-methylbenzoate (1.00 g, 5.42 mmol) in tetrahydrofuran (10 mL) methyl alcohol (5 mL) and water (2.5 mL) is added 2N lithium hydroxide (8.12 mL, 16.2 mmol). The reaction mixture is heated at 50° C. for 2.5 hr, cooled to room temperature, and then quenched with 5N hydrochloric acid (3.24 mL). The mixture is concentrated to remove the tetrahydrofuran and methyl alcohol. A white precipitate is formed and is filtered. After drying, 0.922 g (100%) of 2-chloro-4-methylbenzoic acid is isolated. ES(−)MS m/z 169, (M−H)⁻ consistent with 1 Cl.

Preparation 35

4,4,4-Trifluoro-3-methoxy-but-2-enoic acid ethyl ester

To a solution of ethyl 4,4,4-trifluoroacetoacetate (12 mL, 82 mmol) in DMF (80 mL) is added cesium carbonate (26.4 g, 82 mmol). The reaction mixture is heated to 70° C. A solution of methyl p-toluenesulfonate (13.5 mL, 90 mmol) in DMF (30 mL) is then added dropwise during 30 min and the reaction mixture is stirred for an additional 1 hr. After cooling to room temperature, the reaction mixture is diluted with H₂O (150 mL) and extracted with Et₂O (2×150 mL). The organic extracts are combined and washed with H₂O and brine, then dried (Na₂SO₄), filtered and concentrated to afford the title compound (9.0 g, 56%) as an oil which is used without further purification.

¹H NMR (300 MHz, CDCl₃) δ 1.28 (t, J=7.1 Hz, 3H), 4.01 (s, 3H), 4.19 (q, J=7.1 Hz, 2H), 5.75 (s, 1H)

Preparation 36

3-Hydroxy-5-trifluoromethyl-thiophene-2-carboxylic acid methyl ester

A solution of 4,4,4-trifluoro-3-methoxy-but-2-enoic acid ethyl ester (9.6 g, 48.5 mmol) and methyl thioglycolate (4.3 mL, 48.5 mmol) in MeOH (75 mL) is cooled to 5° C. A solution of KOH (3.3 g, 58.2 mmol) in MeOH (75 mL) is then added over 30 min. The reaction mixture is stirred overnight at room temperature. The reaction mixture is then poured over a stirred mixture of ice (75 g), H₂O (75 mL) and concentrated H₂SO₄ (4.5 mL). The mixture is extracted with EtOAc (2×250 mL). The combined extracts are washed with saturated NaHCO₃. The washings are back-extracted with EtOAc. The combined organic layers are washed with brine, then dried (Na₂SO₄), filtered and concentrated to afford the title compound (10 g, 91%) as a brown oil which is used without further purification.

¹H NMR (300 MHz, CDCl₃) δ 3.92 (s, 3H), 7.06 (s, 1H), 9.48 (br s, 1H)

Preparation 37

3-Hydroxy-5-trifluoromethyl-thiophene-2-carboxylic acid

To a stirred solution of NaOH (8.0 g, 200 mmol) in H₂O (25 mL) is added a solution of 3-hydroxy-5-trifluoromethyl-thiophene-2-carboxylic acid methyl ester (11.4 g, 50 mmol) in MeOH (25 mL). The reaction mixture is heated at reflux for 3 hr and then cooled to room temperature. The reaction mixture is concentrated to about half volume and cooled to 5° C. Acidification to pH 1 with concentrated HCl (17 mL) results in a suspension. After stirrng the suspension for 30 min at 5° C., the solids are collected by filtration, washed with H₂O and dried under vacuum to afford the sub-title compound (8.5 g, 79%) as an off-white solid which is used without further purification.

¹H NMR (300 MHz, CDCl₃) δ 7.30 (s, 1H), 11.7 (br s, 2H)

Preparation 38

5-Trifluoromethyl-thiophen-3-ol

3-Hydroxy-5-trifluoromethyl-thiophene-2-carboxylic acid (8.0 g, 37.8 mmol) is placed in a flask and heated to 105° C. under argon. Heating is continued for 2 hr to complete the decarboxylation. Upon cooling, the title compound is obtained (6.8 g, 85%) as a brown oil which is used without further purification.

$^1$H NMR (300 MHz, CDCl$_3$) enol (major) δ 5.01 (br s, 1H), 6.52 (d, J=1.7 Hz), 7.06 (m, 1H)

$^1$H NMR (300 MHz, CDCl$_3$) keto (minor) δ 3.86 (s, 2H), 6.59 (br s, 1H)

Preparation 39

1-Phenyl-5-(5-trifluoromethyl-thiophen-3-yloxy)-1H-tetrazole

A solution of 5-trifluoromethyl-thiophen-3-ol (2.0 g, 11.9 mmol) in dry acetone (480 mL) containing 5-chloro-1-phenyl-1H-tetrazole (2.1 g, 11.9 mmol) and K$_2$CO$_3$ (3.3 g, 23.8 mmol) is maintained at reflux with careful exclusion of moisture overnight. The acetone is removed under reduced pressure and the residue is partitioned between CH$_2$Cl$_2$ (500 mL) and H$_2$O (50 mL). The organic extracts are washed with brine, then dried (Na$_2$SO$_4$), filtered and concentrated. The crude product is chromatographed on silica gel, eluting with EtOAc:Hex (1:80) to afford the title compound (2.5 g, 68%) as a white solid.

$^1$H NMR (300 MHz, CDCl$_3$) δ 7.52-7.61 (m, 4H), 7.73 (d, J=7.7 Hz, 2H), 7.79 (s, 1H)

Preparations 40 and 41

3-(1-Phenyl-1H-tetrazol-5-yloxy)-5-trifluoromethyl-thiophene-2-sulfonamide and 3-[1-(4-Sulfamoyl-phenyl)-1H-tetrazol-5-yloxy]-5-trifluoromethyl-thiophene-2-sulfonamide A solution of chlorosulfonic acid (2 mL, 30 mmol) is placed in a flask and 1-phenyl-5-(5-trifluoromethyl-thiophen-3-yloxy)-1H-tetrazole (100 mg, 0.30 mmol) is added to the solution under a nitrogen atmosphere. The solution was heated to 100° C. for 2 hr. The solution is cooled to 70° C. and thionyl chloride (0.1 mL, 0.33 mmol) is added then the reaction is reheated to 100° C. and stirred for an additional 2 hr. The reaction mixture is poured onto ice dropwise and the solution is extracted with CH$_2$Cl$_2$ (100 mL). The organic layer is washed with brine, then dried (Na$_2$SO$_4$), filtered and concentrated. The residue is dissolved in acetone (5 mL) and is added to a solution of 29% NH$_4$OH (5 mL) and acetone (10 mL) at 0° C. The mixture is stirred at 0° C. for 30 min. The acetone is removed under reduced pressure and the residue is extracted with EtOAc (2×50 mL). The organic extracts are washed with brine, then dried (Na$_2$SO$_4$), filtered and concentrated. The crude product is chromatographed on silica gel, eluting with EtOAc:Hex (1:3) to afford a mixture of the title compounds (91 mg, 65%) as a white solid. In another reaction, the components are separated by chromatography on silica gel eluting with EtOAc:Hex (1:5) and characterized individually.

$^1$H NMR (300 MHz, CD$_3$OD) δ 7.57-7.67 (m, 4H), 7.89 (d, J=5.9 Hz, 2H)

$^1$H NMR (300 MHz, CD$_3$OD) δ 7.96 (d, J=4.2 Hz, 1H), 8.15 (s, 4H)

Preparation 42

5-Trifluoromethyl-thiophene-2-sulfonamide

To a solution of 3-[1-(4-sulfamoyl-phenyl)-1H-tetrazol-5-yloxy]-5-trifluoromethyl-thiophene-2-sulfonamide (210 mg, 0.47 mmol) in benzene (50 mL) is added H$_2$O (2 mL), EtOH (3 mL), formic acid (2 mL) and 10% palladium on carbon (350 mg). The mixture is heated to 80° C. overnight. The reaction mixture is cooled to room temperature and diluted with benzene (50 mL). The reaction mixture is filtered. The benzene layer is dried (Na$_2$SO$_4$), filtered and concentrated. The crude product is chromatographed on silica gel, eluting with EtOAc:Hex (1:10) to afford the title compound (18 mg, 17%) as a white solid.

The same procedure is applied to 3-(1-phenyl-1H-tetrazol-5-yloxy)-5-trifluoromethyl-thiophene-2-sulfonic acid amide to also produce the title compound.

$^1$H NMR (300 MHz, CD$_3$OD) δ 7.56 (d, J=4.0 Hz, 1H), 7.60 (d, J=4.0 Hz, 1H)

ES(−)MS m/z 230, (M−H)$^-$.

General Coupling Procedure

To a stirring solution of the benzoic acid (1.25 eq) in dry dichloromethane (10 mL/mmol), the sulfonamide (1.0 eq) is added in one portion followed by EDC (1.25-1.5 eq) and finally, N,N-[dimethyl]-4-aminopyridine (1.2 eq). The mixture is vigorously stirred under nitrogen for 16 hr, concentrated under reduced pressure, and the residue partitioned between ethyl acetate and water. The organic layer is washed with 1N hydrochloric acid (4 times, 20 mL/mmol), then the combined aqueous phases extracted with ethyl acetate (twice, 20 mL/mmol). The combined organic layers are finally washed with water and saturated aqueous sodium chloride, dried over sodium sulfate, and concentrated under reduced pressure. The residue may be subjected to silica gel chromatography, reversed phase chromatography or crystallization if necessary or desired.

The compounds of EXAMPLES 1-53 are prepared essentially as described in the general coupling procedure.

| Example # | Product | Mass Spectral Data (m/z) |
|---|---|---|
| 1 | N-[4-bromo-2-chlorobenzoyl]-5-chlorothiophene-2-sulfonamide | ES(−)MS m/z 412, (M − H)$^-$ consistent with 1 Br and 2 Cl. |
| 2 | N-[4-chloro-2-methylbenzoyl]-5-bromothiophene-2-sulfonamide | ES(−)MS m/z 392, (M − H)$^-$ consistent with 1 Br and 1 Cl. |
| 3 | N-[4-bromo-2-chlorobenzoyl]-4-bromo-5-chlorothiophene-2-sulfonamide | ES(−)MS m/z 490, (M − H)$^-$ consistent with 2 Br and 2 Cl. |
| 4 | N-[2,4-bis(trifluoromethyl)-benzoyl]-5-chlorothiophene-2-sulfonamide | ES(−)MS m/z 436, (M − H)$^-$ consistent with 1 Cl. |
| 5 | N-[2,4-bis(trifluoromethyl)-benzoyl]-5-bromothiophene-2-sulfonamide | ES(−)MS m/z 480, (M − H)$^-$ consistent with 1 Br. |

-continued

| Example # | Product | Mass Spectral Data (m/z) |
|---|---|---|
| 6 | N-[2,4-dimethylbenzoyl]-5-chlorothiophene-2-sulfonamide | ES(−)MS m/z 328 (M − H)− consistent with 1 Cl. |
| 7 | N-[2-chloro-4-methylbenzoyl]-5-bromothiophene-2-sulfonamide | ES(+)MS m/z 394 (M + H)+ consistent with 1 Br and 1 Cl. |
| 8 | N-[2-chloro-4-methylbenzoyl]-5-chlorothiophene-2-sulfonamide | ES(+)MS m/z 350, (M + H)+ consistent with 2 Cl |
| 9 | N-[4-chloro-2-fluorobenzoyl]-5-bromothiophene-2-sulfonamide | ES(−)MS m/z 396, (M − H)− consistent with 1 Br and 1 Cl |
| 10 | N-[2-bromo-4-methylbenzoyl]-5-bromothiophene-2-sulfonamide | ES(−)MS m/z 438, (M + H)+ consistent with 2 Br. |
| 11 | N-[2-bromo-4-methylbenzoyl]-5-chlorothiophene-2-sulfonamide | ES(+)MS m/z 394, (M + H)+ consistent with 1 Br and 1 Cl. |
| 12 | N-[4-methyl-2-trifluoromethyl-benzoyl]-5-chlorothiophene-2-sulfonamide | ES(−)MS m/z 382, (M − H)− consistent with 1 Cl. |
| 13 | N-[2,4-dichlorobenzoyl]-5-(methylthio)thiophene-2-sulfonamide | ES(−)MS m/z 380, (M − H)− consistent with 2 Cl. |
| 14 | N-[4-chloro-2-methylbenzoyl]-5-(methylthio)thiophene-2-sulfonamide | ES(−)MS m/z 360, (M − H)− consistent with 1 Cl. |
| 15 | N-[4-methyl-2-bromobenzoyl]-5-(methylthio)thiophene-2-sulfonamide | ES(−)MS m/z 404, (M − H)− consistent with 1 Br. |
| 16 | N-[2,4-dichlorobenzoyl]-5-(methyl)thiophene-2-sulfonamide | ES(−)MS m/z 348, (M − H)− consistent with 2 Cl. |
| 17 | N-[2,4-dichlorobenzoyl]-5-(ethyl)thiophene-2-sulfonamide | ES(−)MS m/z 362, (M − H)− consistent with 2 Cl. |
| 18 | N-[2,4-dichlorobenzoyl]-5-(propyl)thiophene-2-sulfonamide | ES(−)MS m/z 376, (M − H)− consistent with 2 Cl. |
| 19 | N-[2,4-dichlorobenzoyl]-5-methoxythiophene-2-sulfonamide | ES(−)MS m/z 364, (M − H)− consistent with 2 Cl. |
| 20 | N-[2,4-dichlorobenzoyl]-5-methoxymethyl-thiophene-2-sulfonamide | ES(−)MS m/z 378 (M − H)− consistent with 2 Cl. |
| 21 | N-[2-methyl-4-bromobenzoyl]-4-bromothiophene-2-sulfonamide | ES(−)MS m/z 436, (M − H)− consistent with 2 Br. |
| 22 | N-[2-methyl-4-chlorobenzoyl]-2-chlorothiazole-5-sulfonamide | ES(−)MS m/z 349, (M − H)− consistent with 2 Cl. |
| 23 | N-[2,4-dichlorobenzoyl]-2-chlorothiazole-5-sulfonamide | ES(−)MS m/z 369, (M − H)− consistent with 3 Cl. |
| 24 | N-[2,4-dichlorobenzoyl]-2-methoxythiazole-5-sulfonamide | ES(−)MS m/z 365, (M − H)− consistent with 2 Cl. |
| 25 | N-[2-methyl-4-chlorobenzoyl]-2-methoxythiazole-5-sulfonamide | ES(−)MS m/z 345, (M − H)− consistent with 1 Cl. |
| 26 | N-[2,4-dichlorobenzoyl]-4,5-dibromothiophene-2-sulfonamide | ES(−)MS m/z 490, (M − H)− consistent with 1 Br and 2 Cl. |
| 27 | N-[4-bromo-2-methylbenzoyl]-4,5-dibromothiophene-2-sulfonamide | ES(−)MS m/z 514, (M − H)− consistent with 3 Br. |
| 28 | N-[4-chloro-2-methylbenzoyl]-5-cyanothiophene-2-sulfonamide | ES(−)MS m/z 341, (M + H)+ consistent with 1 Cl. |
| 29 | N-[4-bromo-2-methylbenzoyl]-5-cyanothiophene-2-sulfonamide | ES(+)MS m/z 385, (M + H)+ consistent with 1 Br. |
| 30 | N-[4-chloro-2-methylbenzoyl]-5-chlorothiophene-2-sulfonamide | ES(+)MS m/z 350, (M + H)+ consistent with 2 Cl. |
| 31 | N-[2-bromo-4-methylbenzoyl]-5-chlorothiophene-2-sulfonamide | ES(−)MS m/z 392, (M − H)− consistent with 1 Br and 1 Cl. |
| 32 | N-[2,4-dibromobenzoyl]-5-bromothiophene-2-sulfonamide | ES(−)MS m/z 500, (M − H)− consistent with 3 Br. |
| 33 | N-[2-bromo-4-chlorobenzoyl]-5-bromothiophene-2-sulfonamide | ES(−)MS m/z 456, (M − H)− consistent with 2 Br and 1 Cl. |
| 34 | N-[2-methyl-4-bromobenzoyl]-4-chlorothiophene-2-sulfonamide | ES(−)MS m/z 392, (M − H)− consistent with 1 Br and 1 Cl. |
| 35 | N-[2,4-dichlorobenzoyl]-4-chlorothiophene-2-sulfonamide | ES(−)MS m/z 368, (M − H)− consistent with 3 Cl. |
| 36 | N-[2,4-dichlorobenzoyl]-4-chloro-5-bromothiophene-2-sulfonamide | ES(−)MS m/z 446, (M − H)− consistent with 1 Br and 3 Cl. |
| 37 | N-[2,4-dichlorobenzoyl]-4-methyl-5-bromothiophene-2-sulfonamide | ES(−)MS m/z 426, (M − H)− consistent with 1 Br and 2 Cl. |
| 38 | N-[2,4-dichlorobenzoyl]-4-methylthiophene-2-sulfonamide | ES(−)MS m/z 348, (M − H)− consistent with 2 Cl. |
| 39 | N-[2-methyl-4-bromobenzoyl]-4-methoxythiophene-2-sulfonamide | ES(−)MS m/z 388, (M − H)− consistent with 1 Br. |
| 40 | N-[2,4-bistrifluoromethylbenzoyl]-4-methylthiophene-2-sulfonamide | ES(−)MS m/z 416, (M − H)−. |
| 41 | N-[2,4-dichlorobenzoyl]-4-methoxythiophene-2-sulfonamide | ES(−)MS m/z 364, (M − H)− consistent with 2 Cl. |
| 42 | N-[2-methyl-4-bromobenzoyl]-4-methylthio-thiophene-2-sulfonamide | ES(−)MS m/z 404, (M − H)− consistent with 1 Br. |

-continued

| Example # | Product | Mass Spectral Data (m/z) |
|---|---|---|
| 43 | N-[2,4-dichlorobenzoyl]-4-methylthio-thiophene-2-sulfonamide | ES(−)MS m/z 380, (M − H)⁻ consistent with 2 Cl. |
| 44 | N-[2,4-bistrifluoro-methylbenzoyl]-4-methoxythiophene-2-sulfonamide | ES(−)MS m/z 432, (M − H)⁻. |
| 45 | N-[2,4-bis(trifluoro-methyl)benzoyl]-4-methylthio-thiophene-2-sulfonamide | ES(−)MS m/z 448, (M − H)⁻. |
| 46 | N-[2,4-dichlorobenzoyl]-4-methylthio-5-bromothiophene-2-sulfonamide | ES(−)MS m/z 458, (M − H)⁻ consistent with 1 Br and 2 Cl |
| 47 | N-[2,4-dichlorobenzoyl]-4-methoxy-5-bromothiophene-2-sulfonamide | ES(−)MS m/z 442, (M − H)⁻ consistent with 1 Br and 2 Cl |
| 48 | N-[2-methyl-4-bromobenzoyl]-4-methoxy-5-bromothiophene-2-sulfonamide | ES(−)MS m/z 466, (M − H)⁻ consistent with 2 Br. |
| 49 | N-[2-methyl-4-bromobenzoyl]-4-methylthio-5-bromothiophene-2-sulfonamide | ES(−)MS m/z 482, (M − H)⁻ consistent with 2 Br. |
| 50 | N-[2,4-dichlorobenzoyl]-2-isopropylthiazole-5-sulfonamide | ES(−)MS m/z 377, (M − H)⁻ consistent with 2 Cl. |
| 51 | N-[2-methyl-4-bromobenzoyl]-2-isopropylthiazole-5-sulfonamide | ES(−)MS m/z 401, (M − H)⁻ consistent with 1 Br. |
| 52 | N-[2-methyl-4-bromobenzoyl]-2-methylthiazole-5-sulfonamide | ES(−)MS m/z 373, (M − H)⁻ consistent with 1 Br. |
| 53 | N-[2,4-dichloro-benzoyl]-5-trifluoromethylthiophene-2-sulfonamide | ES(−)MS m/z 402, (M − H)⁻ consistent with 2 Cl. |

EXAMPLE 54

N-[4-bromo-2-chlorobenzoyl]-5-bromothiophene-2-sulfonamide

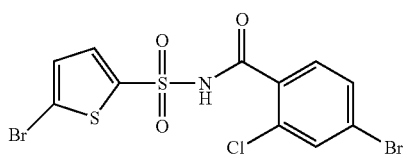

An 8 mL reaction vial is charged with 4-bromo-2-chlorobenzoic acid (0.39 mmol, 1.5 eq) and 2.0 mL of dichloromethane. A stock solution (4.0 mL) containing 5-bromothiophene-2-sulfonamide (0.26 mmol, 1 eq) and N,N-[dimethyl]-4-aminopyridine (48 mg, 0.39 mmol, 1.5 eq) in dichloromethane is added, followed by 0.261 g carbodiimide polystyrene resin (2.0 mmol/g, 0.52 mmol, 2.0 eq, Novabiochem) and the vial is capped and shaken. After 72 hr, 0.77 g sulphonated polystyrene resin (MP-TsOH) is added (1.53 mmol/g, 1.17 mmol, Argonaut). After about 18 hr the reaction mixture is filtered and concentrated under reduced pressure. Chromatography was applied to the residue and fractions containing product were combined and concentrated under reduced pressure to provide the title compound.

ES(−)MS m/z 456, (M−H)⁻ consistent with 2 Br and 1 Cl.

The compounds of Examples 55-62 are prepared essentially as described in Example 54.

| Example # | Product | Mass Spectral Data (m/z) |
|---|---|---|
| 55 | N-[2,4-dichlorobenzoyl]-thiophene-2-sulfonamide | ES(−)MS m/z 334, (M − H)⁻ consistent with 2 Cl. |
| 56 | N-[2,4-dichlorobenzoyl]-5-(2-pyridyl)-thiophene-2-sulfonamide | ES(−)MS m/z 411, (M − H)⁻ consistent with 2 Cl. |
| 57 | N-[4-bromo-2-methylbenzoyl]-5-bromothiophene-2-sulfonamide | ES(−)MS m/z 436, (M − H)⁻ consistent with 2 Br. |
| 58 | N-[2-chloro-4-nitrobenzoyl]-5-bromothiophene-2-sulfonamide | ES(−)MS m/z 423, (M − H)⁻ consistent with 1 Br and 1 Cl. |
| 59 | N-[2,4-dimethylbenzoyl]-5-bromothiophene-2-sulfonamide | ES(−)MS m/z 372, (M − H)⁻ consistent with 1 Br. |
| 60 | N-[4-chloro-2-methylbenzoyl]-5-chlorothiophene-2-sulfonamide | ES(−)MS m/z 348, (M − H)⁻ consistent with 2 Cl. |
| 61 | N-[2,4-dichlorobenzoyl]-5-chlorothiophene-2-sulfonamide | ES(−)MS m/z 368, (M − H)⁻ consistent with 3 Cl. |
| 62 | N-[2,4-dichlorobenzoyl]-5-(phenylthio)thiophene-2-sulfonamide | ES(−)MS m/z 442, (M − H)⁻ consistent with 2 Cl. |

EXAMPLE 63

N-[2,4-dichlorobenzoyl]-5-bromothiophene-2-sulfonamide

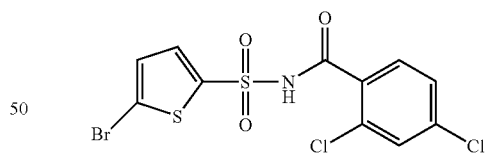

To a reaction mixture of dichlorobenzoic acid (28.4 g, 148.7 mmol), 5-bromo-2-sulfonamide (30.0 g, 123.9 mmol) and EtOAc (200.0 mL) at room temperature is added a hot solution of CDI (24.1 g, 148.7 mmol) in THF (100.0 mL) over a period of 13.0 min. Extra THF (50.0 mL) is added to aid and wash residual CDI into the reaction vessel. Gas evolution is observed during addition of CDI solution/slurry. This can be controlled by the rate of addition. At the end of CDI addition, the light yellow solution is stirred for 10 min, and then heated at reflux for 90 min or until no gas evolution is observed (reaction intermediate is monitored by GC and deemed complete when no acid peak is observed). The reaction is then allowed to equilibrate to 40° C. after which neat DBU (22.3 mL, 148.7 mm) is added all at once (maximum temperature attained by the end of addition is 45° C.) and stirred to room temperature overnight for convenience. The reaction is deemed complete by HPLC with the disappearance of the sulfonamide starting material. Deionized water (250.0 mL) is then added and the top organic layer separated. The aqueous layer is back extracted with EtOAc (50. mL). The combined organic layers are washed vigorously with 1N HCl solution (500.0 ml), dried with anhydrous MgSO$_4$, filtered and the cake washed with EtOAc (20.0 mL). The filtrate is then concentrated at reduced pressure (water bath temp. ~50° C.) to 70.4 g of a thick solution. To this solution is added heptane (200.0 mL) with vigorous stirring until an off-white precipitate forms in about an hour. The precipitate is filtered and the cake washed with heptane (25.0 mL). The precipitate is then dried in a house vacuum at 55° C. for 18 hr (45.4 g, 88.2% wt yield). ES(−)MS m/z 412, (M−H)⁻ consistent with 1 Br and 2 Cl.

EXAMPLE 64

N-[2,4-dichlorobenzoyl]-5-bromothiophene-2-sulfonamide sodium salt

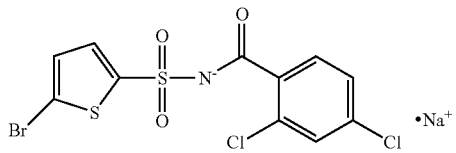

To a solution of the compound of Example 63 (25.0 g, 60.2 mmol) and MTBE (208.0 mL) at room temperature is added sodium methoxide (3.3 g, 60.2 mmol) in a single portion. The reaction is then stirred for 24 hr, after which heptane (426.0 ml) is added followed by vigorous stirring for 60 min. A white precipitate forms and is then filtered under a positive nitrogen pressure, and the cake subsequently washed with heptane (150.0 mL). The precipitate is then pulled to semi-dryness, followed by drying in a house vacuum oven at 100° C. for 18 hr (mass=22.1 g, 84% wt. Yield; $^1$H NMR (DMSO d$_6$) 7.13-7.14δ (d, J=3.9 Hz, 1H), 7.30-7.35 (m, 2H), 7.47-7.52 (m, 2H)).

All of the compounds concerned are orally available and are normally administered orally, and so oral administration is preferred. However, oral administration is not the only route or even the only preferred route. For example, transdermal administration is very desirable for patients who are forgetful or petulant about taking oral medicine, and the intravenous route may be preferred as a matter of convenience or to avoid potential complications related to oral administration. Compounds of Formula I may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations preferably contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, steric acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

Injections for parenteral administration include sterile aqueous or non-aqueous solutions, suspensions and emulsions. Aqueous solutions and suspensions may include distilled water for injection or physiological salt solution. Non-aqueous solutions and suspensions may include propylene glycol, polyethylene glycol, vegetable oil such as olive oil, alcohol such as ethanol or POLYSORBATE80 (registered trade mark). Injections may comprise additional ingredients other than inert diluents: e.g. preserving agents, wetting agents, emulsifying agents, dispersing agents, stabilizing agents (such as lactose), assisting agents such as agents to assist dissolution (e.g. glutamic acid or aspartic acid). They may be sterilized for example, by filtration through a bacteria-retaining filter, by incorporation of sterilizing agents in the compositions or by irradiation. They may also be manufactured in the form of sterile solid compositions that may be dissolved in sterile water or some other sterile diluent(s) for injection immediately before use.

The compounds of Formula I are generally effective over a wide dosage range. For example, dosages per day normally fall within the range of about 10 to about 300 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

Inhibition of HUVEC Proliferation

Human umbilical vein endothelial cells (HUVEC; Bio-Whittaker/Clonetics, Walkersville, Md.) were maintained in endothelial cell growth medium (EGM) containing basal medium (EBM) with bovine brain extract, human epidermal growth factor, hydrocortisone, gentamicin, amphotericin B and 2% fetal bovine serum. For the assay, HUVEC ($5\times10^3$) in EBM (200 µl) with 0.5% fetal bovine serum were added to wells in a 96-well cell culture plate and incubated at 37° C. for 24 hr in humidified 5% carbon dioxide/air. The test compounds were serially diluted in dimethyl sulfoxide (DMSO) in concentrations from 0.0013 to 40 µM and added to the wells in 20 µl. Then human vascular endothelial growth factor (VEGF) (20 ng/ml in wells; R&D Systems, Minneapolis, Minn.) prepared from a stock solution of 100 µg/ml in phosphate buffered normal saline containing 0.1% bovine serum albumin, was added to the wells. The HUVEC were incubated at 37° C. for 72 hr in humidified 5% carbon dioxide/air. WST-1 cell proliferation reagent (20 µl; Boehringer Mannheim, Indianapolis, Ind.) was added to the wells and the plates returned to the incubator for 1 hr. The absorbance of each well at 440 nm was measured. The growth fraction was determined from the absorbance of treated wells with and without VEGF divided by the absorbance obtained from control wells set to zero and 1.0. The exemplified compounds were tested in this assay and all exhibited an $IC_{50} \leq 1.0$ µM.

HCT116 Colon Carcinoma Cell Growth Inhibition

Human HCT 116 colon carcinoma cells were grown monolayer culture in RPMI 1640 medium supplemented with 10% fetal bovine serum and 1% penicillin-streptomycin (GibcoBRL, Grand Island, N.Y.). HCT116 cells in exponential growth phase were exposed to various concentrations of the test compounds at 37° C. for 72 hr in 5% carbon dioxide/air. After exposure to the agent, the cells were washed with 0.9% phosphate buffered saline. Growth inhibition was determined using WST-1 cell proliferation reagent as described above. The results are expressed as the growth fraction of treated cells compared with control cultures. Representative compounds of the present invention were tested for efficacy against the human colon HCT116 tumor cells. The data from these experiments are summarized in TABLE 1.

TABLE I

| Human Colon HCT116 tumor cells | |
| --- | --- |
| EXAMPLE | $IC_{50}$ (µM) |
| 1 | 5.6 |
| 2 | 6.0 |
| 3 | 14.7 |
| 4 | 7.7 |
| 6 | 20.6 |
| 7 | 5.2 |
| 9 | 21.7 |
| 16 | 3.7 |
| 17 | 5.0 |
| 18 | 13.2 |

TABLE I-continued

| Human Colon HCT116 tumor cells | |
| --- | --- |
| EXAMPLE | $IC_{50}$ (µM) |
| 19 | 5.8 |
| 20 | 5.7 |
| 28 | 8.0 |
| 29 | 17.3 |
| 30 | 15.8 |
| 31 | 9.1 |
| 32 | 3.9 |
| 54 | 17.0 |
| 55 | 4.5 |
| 56 | 5.4 |
| 57 | 3.4 |
| 58 | 5.2 |
| 61 | 1.0 |
| 63 | 1.3 |

Conventional Murine Tumor and Human Tumor Xenograft Assays

Inhibition of tumors transplanted into mice is an accepted procedure for studying the efficacy of antitumor agents (Corbett, et al., *In vivo Methods for Screening and Preclinical Testing; Use of rodent solid tumors for drug discovery.*, In: Anticancer Drug Development Guide: Preclinical Screening, Clinical Trials, and Approval, B. Teicher (ed), Humana Press Inc., Totowa, N.J., Chapter 5, pages 75-99 (1997); (Corbett, et al., Int. *J. Pharmacog.*, 33, Supplement, 102-122 (1995)). Murine tumors or human xenografts were implanted essentially as described by Corbett in *In vivo Methods for Screening and Preclinical Testing; Use of rodent solid tumors for drug discovery*. Briefly, the murine tumor or human xenograft was implanted subcutaneously using either 12-gauge trocar implants or counted number of cells. The location for the trocar insertion is midway between the axillary and inguinal region along the side of the mouse. The trocar is slipped approximately ¾ of an inch subcutaneously up toward the axilla before discharging the tumor fragment, and pinching the skin as the trocar is removed. Alternatively, human tumor cells prepared from cell culture ($1\times10^7$ cells) mixed with an equal volume of Matrigel (Becton-Dickinson) were implanted subcutaneously in a hind-leg of a male or female nude mouse (Charles River). A test compound in vehicle or vehicle alone was administered by intravenous bolus injection (iv), intraperitoneal injection (ip), or oral gavage (po). Each treatment group, as well as a group of untreated control animals, consisted of eight to ten animals per group in each experiment. Subcutaneous tumor response was monitored by tumor volume measurement performed twice each week over the course of the experiment (60-120 days). Body weights were taken as a general measure of toxicity. The subcutaneous tumor data were analyzed by determining the median tumor weight for each treatment group over the course of the experiment and calculating the tumor growth delay as the difference in days for the treatment versus the control tumors to reach a volume of either 500 or 1000 mm$^3$.

The compound of Example 64 was tested in two separate laboratories against a variety of murine and human tumors substantially as described supra. The data from these tests are summarized in TABLE II. The parameters measured in each experiment are summarized in the following paragraphs.

Tumor Weight(mg)=$(a \times b^2)/2$ where $a$=tumor length (mm) and $b$=tumor width (mm).

Tumor Growth Delay=$T$-$C$ where $T$ is the median time (days) required for the treatment group tumors to reach a predetermined size, and $C$ is the median time (days) for the control group tumors to reach the same size.

TABLE II

Human Colon Carcinoma HT-29

| Example 64 | Dose (mg/kg) | Tumor Growth Delay (d) |
| --- | --- | --- |
| Experiment A | 30 | 0 +/− 2 |
| | 60 | 2 +/− 2 |
| | 80 | 2 +/− 2 |
| Experiment B | 30 | 9 +/− 4 |
| | 60 | 3 +/− 4 |
| | 80 | 8 +/− 3.6 |

After palpable tumors were observed drug was administered IV for 5 consecutive days, animals rested for 2 days and compound dosed IV again for 5 consecutive days.

We claim:

1. A method of treating a susceptible neoplasm selected from the group consisting of metastatic soft tissue sarcoma, non-small cell lung cancer, melanoma, ovarian cancer, breast cancer, leukemia, lymphoma, renal cancer, prostate cancer, and multiple myeloma in a mammal comprising administering to a mammal in need of such treatment an oncolytically effective amount of a compound of Formula I:

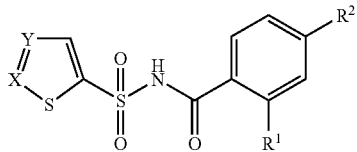

where:

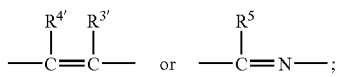

—X=Y— is $R^1$ is selected from the group consisting of halo, $C_1$-$C_6$ alkyl, and $CF_3$;

$R^2$ is selected from the group consisting of halo, —$NO_2$, $C_1$-$C_6$ alkyl, and $CF_3$;

$R^{3'}$ is H, $C_1$-$C_6$ alkyl, $C_1$-$C_4$ alkoxy, $C_1$-$C_6$ alkylthio, or halo;

$R^{4'}$ is selected from the group consisting of H, halo, $C_1$-$C_4$ alkoxy, —COO($C_1$-$C_6$ alkyl), $C_1$-$C_6$ alkyl optionally substituted with $C_1$-$C_4$ alkoxy, cyano, $C_1$-$C_6$ alkylthio, $CF_3$, S-phenyl, and pyridinyl;

$R^5$ is halo, $C_1$-$C_6$ alkyl, or $C_1$-$C_4$ alkoxy; or a pharmaceutically acceptable base addition salt thereof.

2. The method of claim 1 wherein the compound is N-[2,4-dichlorobenzoyl]-5-bromothiophene-2-sulfonamide or a pharmaceutically acceptable base addition salt thereof.

3. The method of claim 2 wherein the compound is N-[2,4-dichlorobenzoyl]-5-bromothiophene-2-sulfonamide sodium salt.

4. The method of claim 1 wherein the susceptible neoplasm is selected from the group consisting of metastatic soft tissue sarcoma, non-small cell lung cancer, melanoma, and ovarian cancer.

5. The method of claim 4 wherein the compound is N-[2,4-dichlorobenzoyl]-5-bromothiophene-2-sulfonamide or a pharmaceutically acceptable base addition salt thereof.

6. The method of claim 5 wherein the compound is N-[2,4-dichlorobenzoyl]-5-bromothiophene-2-sulfonamide sodium salt.

* * * * *

UNITED STATES PATENT AND TRADEMARK OFFICE
CERTIFICATE OF CORRECTION

PATENT NO.         : 7,250,430 B2
APPLICATION NO. : 11/447457
DATED              : July 31, 2007
INVENTOR(S)        : Grossman et al.

Page 1 of 1

It is certified that error appears in the above-identified patent and that said Letters Patent is hereby corrected as shown below:

On the Title Page, Item (60) under related application data, please insert,

--This application is a continuation of U.S. Patent Application 10/490,935 filed on October 15, 2002, which is now US patent 7,084,170 that issued on August 1, 2006, which claims priority to US provisional 60/352,012 filed on October 25, 2001.--

Signed and Sealed this

Eighteenth Day of August, 2009

David J. Kappos
*Director of the United States Patent and Trademark Office*